United States Patent [19]

Omori et al.

[11] Patent Number: 5,066,915
[45] Date of Patent: Nov. 19, 1991

[54] RF COIL POSITIONING DEVICE FOR MRI

[75] Inventors: Katsuhisa Omori, Atsugi; Masaya Yamashita, Hiratsuka, both of Japan

[73] Assignee: Siemens-Asahi Medical System, Ltd., Tokyo, Japan

[21] Appl. No.: 540,720

[22] Filed: Jun. 20, 1990

[30] Foreign Application Priority Data

Jun. 28, 1989 [JP] Japan .................................. 64-167494

[51] Int. Cl.⁵ .............................................. G01R 33/20
[52] U.S. Cl. ................................................... 324/318
[58] Field of Search ................... 128/653 A; 335/216, 335/219; 324/318, 309, 322

[56] References Cited

U.S. PATENT DOCUMENTS

| | | | |
|---|---|---|---|
| 4,629,989 | 12/1986 | Riehl et al. | 324/318 |
| 4,727,328 | 2/1988 | Carper et al. | 324/318 |
| 4,771,785 | 9/1988 | Duer | 128/653 |
| 4,791,371 | 12/1988 | Krol | 324/318 |
| 4,972,852 | 11/1990 | Koob et al. | 128/653 R |

Primary Examiner—Michael J. Tokar
Attorney, Agent, or Firm—Sughrue, Mion, Zinn, Macpeak & Seas

[57] ABSTRACT

An RF coil positioning device for MRI in which a pallet of a bed unit of an MRI device is moved so that an RF coil unit mounted on the pallet is positioned at the center of a magnetostatic field of the magnetostatic field generator, includes: a coil detector provided at a predetermined position along a path of the pallet, for detecting the passage of the RF coil unit through a reference position; an encoder for detecting the distance of travel of the pallet; and control circuit for controlling the drive of the motor so that the pallet is moved until the distance of travel of the pallet after the generation of a detection signal from the coil detector and the distance from the reference position to the center of the magnetostatic field become equal to each other.

18 Claims, 7 Drawing Sheets

RF COIL POSITIONING DEVICE FOR MRI

BACKGROUND OF THE INVENTION

The present invention relates to a device for moving and positioning an RF coil of an MRI (Magnetic Resonance Imaging or nuclear magnetic resonance-CT) device at an imaging position in a magnetostatic field.

With conventional X-ray CT (Computed Tomography) it is necessary, for determining the position of imaging an examinee, that a specified region of his body which is desired to be imaged be set at an optical marker fixed at a reference position. The optical marker is, for example, a cross-shaped light image projected onto the skin surface of the examinee.

Also in an MRI device of the type in which the RF coil is fixed at the center of a magnetostatic field generator, the above-mentioned specified region of the examinee lying on a movable pallet is set at an optical marker fixed at a reference position outside the magnetostatic field generator and then the pallet is moved a predetermined distance to bring the specified region to the center of the RF coil. In this instance, the RF coil must be made large to such an extent that the examinee carried on the pallet will not bump against the coil disposed in the magnetostatic field generator—this impairs the MR signal detecting sensitivity. Further, much labor and time are consumed for setting the optical marker at the specified region to be imaged while moving the pallet with the examinee thereon.

In an MRI device of the type in which an operator attaches the RF coil to the pallet in accordance with the specified region of the examinee's body on the pallet, the pallet is moved until the center of the RF coil attached to the pallet is brought to the vicinity of the position of an optical marker fixedly disposed, for example, at the inlet of the magnetostatic field generator, and thereafter the center of the RF coil is aligned accurately with the position of the optical marker, after which a drive start signal is applied to a pallet drive control unit to move the pallet a predetermined distance, thereby bringing the RF coil to the center of the magnetostatic field (i.e. the imaging position). In this case, since the RF coil is disposed in accordance with the specified region of the examinee's body to be imaged, the RF coil can be made relatively small; so that the MR signal detecting sensitivity can be increased. However, the performance of the MRI device is seriously degraded unless the center of the RF coil is accurately set at the center of the magnetostatic field. Accordingly, an appreciable amount of time is needed for setting the center of the RF coil at the position of the optical marker while carrying the examinee on the pallet as in the above-mentioned example, and in addition, much skill is required for such an operation.

In Japanese Patent Application Laid Open No. 1-284290 there is disclosed an MRI device which is free from the above-mentioned defects and permits easy positioning of a specified region of the examinee's body. In this device a slidable positioning piece is provided in a groove formed along one marginal edge of the pallet and a light sensor is disposed on an inner wall centrally of the magnetostatic field. The operator starts the pallet drive unit after sliding the positioning piece to set it at the specified region of the examinee's body on the pallet. The pallet drive unit stops the pallet from moving at the point of time when the light sensor optically detects the positioning piece. It is not described whether the RF coil is fixed at the center of the magnetostatic field or mounted on the pallet, but at any rate, the pallet carrying the examinee need not be moved for positioning the specified region of the examinee's body. In the case where this device is employed for positioning an RF coil, however, since the positioning piece is aligned with the specific region to be imaged through eye measurement, accurate positioning of the RF coil is difficult. Moreover, the method of stopping the pallet upon detection of the positioning piece is basically braking control, and in practice, the pallet does not always stop at a target position but its stopping position scatters according to the examinee's weight as well. In view of this, it is recommended in the afore-mentioned literature to selectively employ the optical marker or the positioning contact piece in dependence on whether the positioning accuracy required is high or not, but the individual methods which are selectively used still each have the afore-mentioned defect of its own.

SUMMARY OF THE INVENTION

It is therefore an object of the present invention to provide an RF coil positioning device for MRI which enables the RF coil on the pallet to be accurately positioned at the imaging position in the magnetostatic field in a short time.

The RF coil positioning device of the present invention includes: coil detecting means provided on a path between an initial position of the RF coil and the imaging position, for detecting an RF coil unit which passes through a reference position at a preknown distance from the imaging position; distance detecting means for detecting the distance of travel of the pallet; and drive control means for controlling the motor drive to move the pallet until the distance of its travel after the production of a detection signal from the coil detecting means becomes equal to the above-mentioned preknown distance from the reference position to the imaging position.

Since the motor drive is thus controlled based on the distance the pallet has actually moved, the pallet can be moved from any initial position, besides the RF coil can be brought to and positioned at the imaging position without the necessity of positioning it at the reference position.

DESCRIPTION OF THE PREFERRED EMBODIMENT

Figure 1:
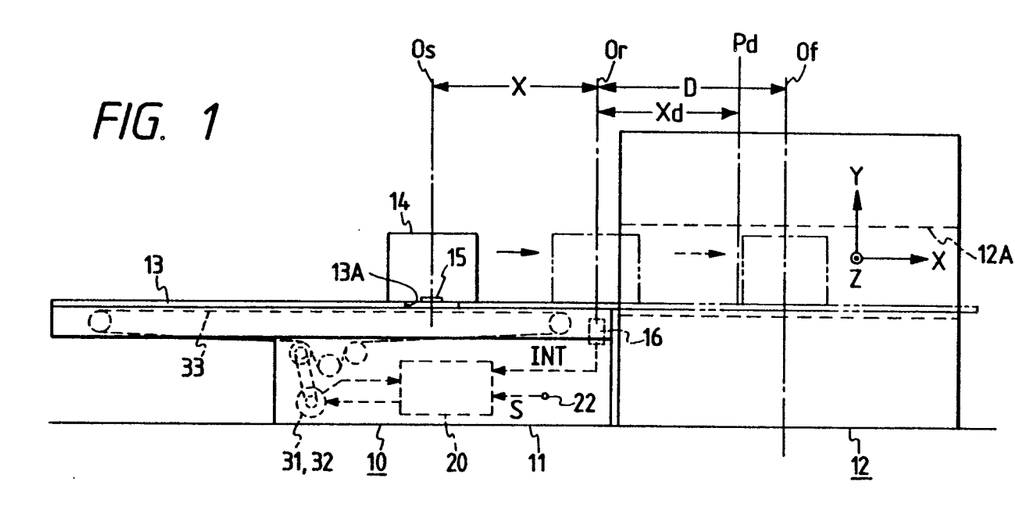
FIG. 1 is a diagram showing the basic construction of an MRI device, for explaining an embodiment of the present invention.

FIG. 1 illustrates the basic construction of the MRI device, for explaining an embodiment of the present invention, in which a bed unit 10 and a magnetostatic field generator 12 are provided adjacent to each other. The bed unit 10 includes a fixed mount 11 and a pallet 13 movably mounted thereon. In FIG. 1 the pallet 13 is shown to be movable in the X-axis direction. The pallet 13 carrying an examinee (not shown) and an RF coil unit 14 is moved on the mount 11 so that the examinee and the RF coil unit 14 are placed in a magnetic field compartment 12A of the magnetostatic field generator 12. The RF coil unit 14 is mounted on the pallet 13 in accordance with the specified region of the examinee's body to be imaged. In FIG. 1 the magnetic field compartment 12A is shown to extend in the X-axis direction and the magnetostatic field is generated in, for example, the Z-axis direction. i.e. in the direction normal to the plane of the drawing.

In the present invention a reflection type photoelectric sensor 16 is provided for detecting the RF coil unit 14 when it reaches a predetermined reference position Or in the X-axis direction on the RF coil unit path between an initial position Os of the RF coil unit 14 and an imaging position in the magnetic field compartment 12A (the center Of of the magnetic field compartment 12A in the X-axis direction). For this detection a reflecting mirror 15 is mounted on the underside of the RF coil unit 14 in this example. On the other hand, the reflection type photoelectric sensor 16 is fixedly mounted, as a coil detector, on the mount 11 below the underside of the pallet 13 so that it faces the reflecting mirror 15 when the latter reaches the reference position Or. The position of the photoelectric sensor 16 is adjusted so that when the reflecting mirror 15 has reached the reference position Or, light from the photoelectric sensor 16 is reflected back thereto by the reflecting mirror 15 to thereby detect that the RF coil unit 14 has reached the reference position Or.

Since this embodiment employs an optical detecting means as the coil detector 16 as mentioned above, the pallet 13 has a slot window 13A corresponding to the reflecting mirror 15 and covered with glass or an acrylic material, for instance. In order that the position where to dispose the RF coil unit 14 on the pallet 13 may be selected as desired, the portion of the pallet 13 which corresponds to the photoelectric sensor 16 is made transparent along the entire length of the pallet 13, or the pallet 13 is made transparent at regular intervals in the X-axis direction so that the RF coil unit 14 can be selectively disposed.

The coil detector 16 may be a proximity switch, a limit switch and a transmission type photoelectric sensor as well as the reflection type photoelectric sensor, but in view of the high-intensity magnetostatic field inside and outside of the magnetostatic field generator 12, the reflection type photoelectric sensor is optimum. The reference position Or may be determined so that the photoelectric sensor 16 is placed inside the magnetostatic field generator 12, but the photoelectric sensor 16 may preferably be disposed outside the magnetostatic field generator 12 as shown in FIG. 1 so as to make the magnetostatic field as homogeneous as possible.

The reflecting mirror 15 may be mounted on the RF coil unit 14 at any desired position, but since there are a wide variety of RF coil units, it is preferable that the reflecting mirror 15 be mounted on the RF coil unit 14 with the center of edge of the former set at the center of the latter in the X-axis direction so that the center of the RF coil can be set at the center position Of of the magnetic field compartment 12A by moving it the same distance from the reference position Or irrespective of the kind of RF coil unit 14 being used. Moreover, in the case where the reflecting mirror 15 is mounted on the underside of the RF coil unit 14 facing the pallet 13 and the photoelectric sensor 16 is disposed below the pallet 13 as shown in FIG. 1, there is no fear of the examinee inadvertently hindering the detecting operation of the photoelectric sensor 16 or false reflected light being applied to the photoelectric sensor 16.

Figure 2:
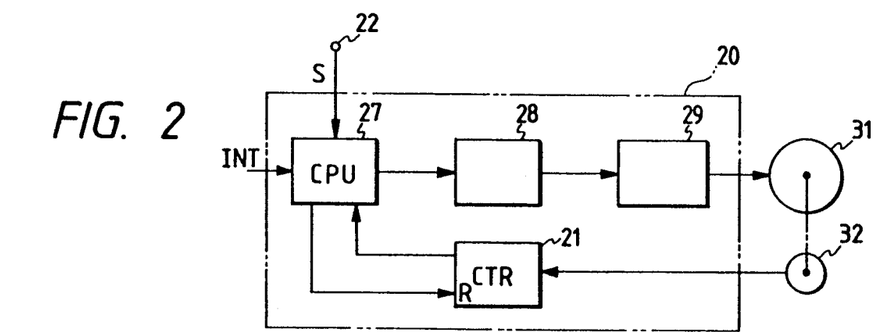
FIG. 2 is a block diagram illustrating a pallet drive control unit for moving and positioning an RF coil.

FIG. 2 illustrates a pallet drive unit for moving the pallet 13 in FIG. 1. The pallet drive unit is disposed inside the mount 11 and is composed of a control circuit 20, a stepping motor 31 which is driven by the control circuit 20, and a rotary encoder 32 for detecting the distance of travel of the pallet 13. The motor 31 drives a belt 33, by which the pallet 13 coupled with the belt 33 can be moved in the X-axis direction. The control circuit 20 includes a CPU 27, a pulse generator 28 placed under control of the CPU 27, a motor driver 29 which drives the motor 31 by a rotational angle corresponding to the number of pulses emanating from the pulse generator 28, and a counter 21 for counting pulses from the encoder 32.

The pulse generator 28 responds to a command of the CPU 27 to generate pulses, which are applied to the driver 29 to cause it to drive the stepping motor 31 and hence move the pallet 13. For each unit distance of travel of the pallet 13 (corresponding to the unit rotational angle of the motor 31) the encoder 32 generates a pulse, which is counted by the counter 21. The count value of the counter 21 is provided to the CPU 27. In this embodiment the pallet 13 is driven by the stepping motor 31, but a servomotor, DC motor or the like may be used to drive the pallet 13.

Next, a description will be given, with reference to FIGS. 1 and 2, of an operation for moving the RF coil unit 14 to the imaging position Of in the magnetic field compartment 12A.

At first, the RF coil 14 and the examinee are put on the pallet 13 such that the RF coil unit 14 is located at the position corresponding to the specified region of the examinee's to be imaged. Then, a start signal S is applied from the outside to a terminal 22, to which the CPU 27 responds to provide a pulse generation start instruction to the pulse generator 28. When supplied with the pulse generation start instruction, the pulse generator 28 generates pulses so that the frequency increases at a fixed rate up to a value prespecified by the CPU 27. The motor driver 29 responds to each pulse from the pulse generator 28 to turn the stepping motor 31 by one step. Hence, the motor 31 gradually increases its rotating speed as pulses are generated by the pulse generator 28, and when a predetermined speed is reached, the motor 31 is held at this speed. The belt 22 is driven by the rotation of the stepping motor 31, by which the pallet 13 is brought into the magnetic field compartment 12A of the magnetostatic field generator 12.

When the RF coil unit 14 passes through the reference position Or, it is detected by the reflecting mirror 15 and the photoelectric sensor 16, and an interrupt signal INT is applied from the photoelectric sensor 16 to the CPU 27. Upon receipt of the interrupt signal INT, the CPU 27 provides a reset signal to the counter 21 to reset its contents. Consequently, the counter 21 measures the distance of travel of the RF coil unit 14 from the reference position Or. After receiving the interrupt signal INT the CPU 27 fetches the count value of the counter 21 at a fixed cycle, compares the count value with a distance Xd from the reference position Or to a predetermined position Pd short of the imaging position Of and, when the count value agrees with the distance Xd, provides a stop instruction to the pulse generator 28. Upon receipt of the stop instruction, the pulse generator 28 gradually decreases the pulse generating frequency to zero at a fixed rate so that the movement of the pallet 13 starts deceleration at the position Pd and stops at the imaging position Of.

The following position correcting operation may also be effected as required. That is, the CPU 27 compares the count value of the counter 21, i.e. the distance from the reference position Or to the halt position with the distance D from the reference position Or to the imaging position Of, and when the count value has not reached the distance D, the CPU 27 calculates the difference between them and provides it to the pulse generator 28. The pulse generator 28 produces, at a predetermined low frequency, pulses of the number corresponding to the above difference and applies the pulses to the motor driver 29.

Although in the above the measurement of the distance of travel is started at the reference position Or for controlling the travel of the pallet 13, it is also possible to measure the distance of travel from the initial position Os as described hereunder.

At first, the RF coil 14 and the examinee are put on the pallet 13 such that the RF coil unit 14 is located at the position corresponding to the specified region of the examinee's to be imaged. Then the start signal S is applied to the terminal 22. The CPU 27 responds to the start signal S to apply a reset signal to the counter 21 to reset its contents and, at the same time, the CPU 27 sets in an internal register (not shown) of the pulse generator 28, as the distance to a provisional target halt position, a predetermined value C larger than a maximum value of an estimated distance from the initial position Os to the reference position Or. The pulse generator 28 starts to generate pulses towards the preset pulse number C and the driver 29 responds to the pulses to drive the stepping motor 31. The stepping motor 31 drives the belt 33, by which the pallet 13 enters into the magnetic field compartment 12A of the magnetostatic field generator 12. The initial position Os of the RF coil unit 14 may be arbitrary.

When the RF coil unit 14 passes through the reference position Or, it is detected by the reflecting mirror 15 and the photoelectric sensor 16. The photoelectric sensor 16 applies the interrupt signal INT to the CPU 27. When receiving the interrupt signal INT, the CPU 27 reads out of the counter 21 the number of pulses from the encoder 32 counted by the counter 21 until then, that is, the distance X of travel of the pallet 13, and calculates the sum of the value X and the predetermined distance D from the reference position Or to the imaging position Of. The sum is provided, as the distance from the initial position Os to the final halt position, that is, the imaging position Of, to the pulse generator 28, and the contents of its internal register are updated with the value of the sum, changing the target halt position. Accordingly, the pulse generator 28 controls the driver 29 so that the pallet 13 stops when the RF coil unit 14 has reached the final halt position Of. In consequence, the center of the RF coil unit 14 is positioned at the center of the magnetic field compartment 12A (i.e. the imaging position Of). It is also possible to employ an arrangement in which when the pallet 13 is stopped, the CPU 27 reads out of the counter 21 the distance the pallet has moved until then, and compares the distance with the precalculated distance to the final halt position, and when the final halt position has not been reached, the difference is provided to the pulse generator 28 for correcting the position of the pallet 13.

Figure 3:
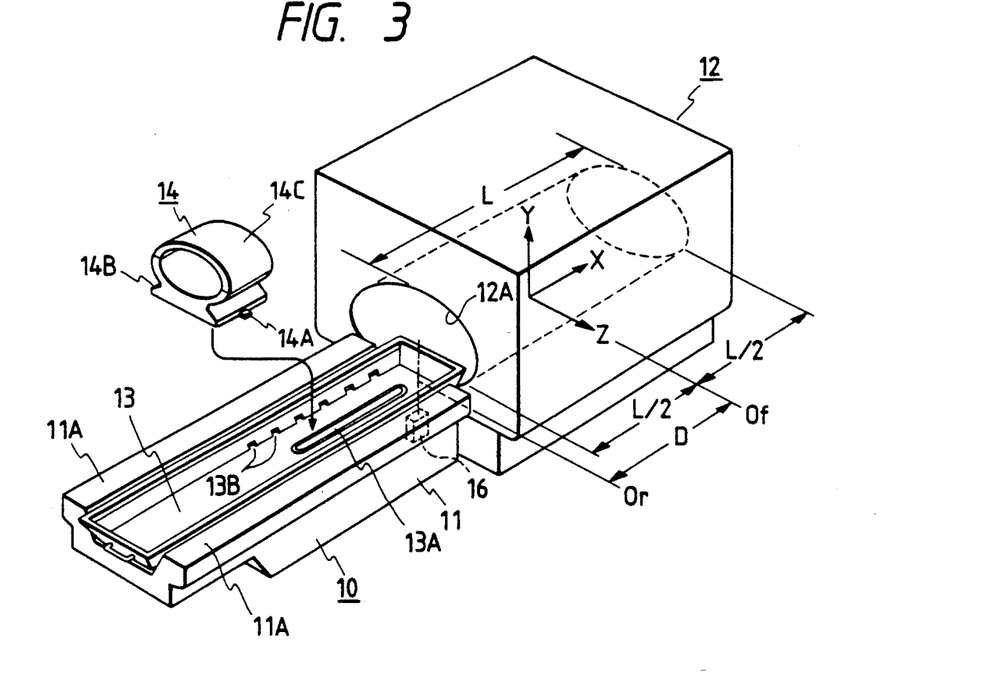
FIG. 3 is a perspective view of the MRI device, for explaining a specific operative example of the present invention.
Figure 4:
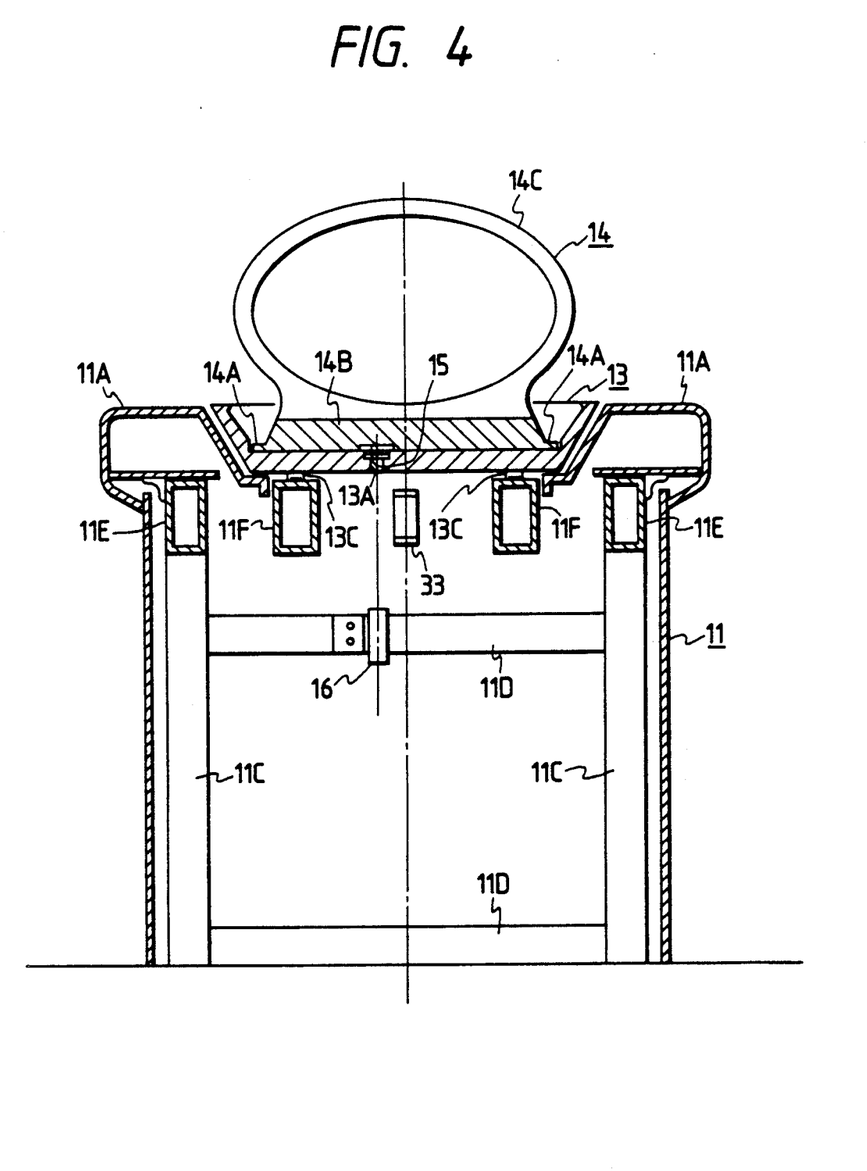
FIG. 4 is a cross-sectional view of a bed unit in FIG. 3.
Figure 5:
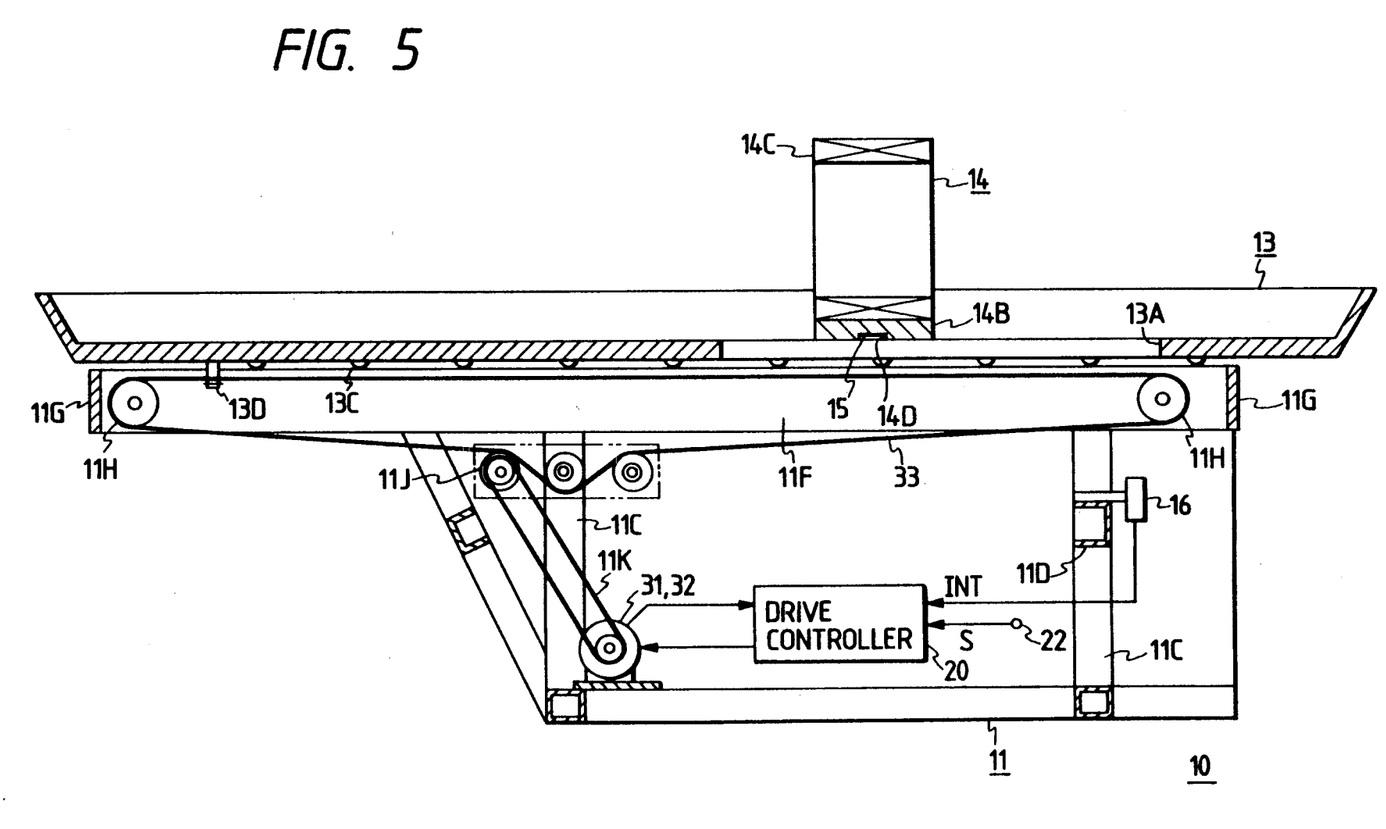
FIG. 5 is a longitudinal sectional view of the bed unit in FIG. 3.
Figure 6A:
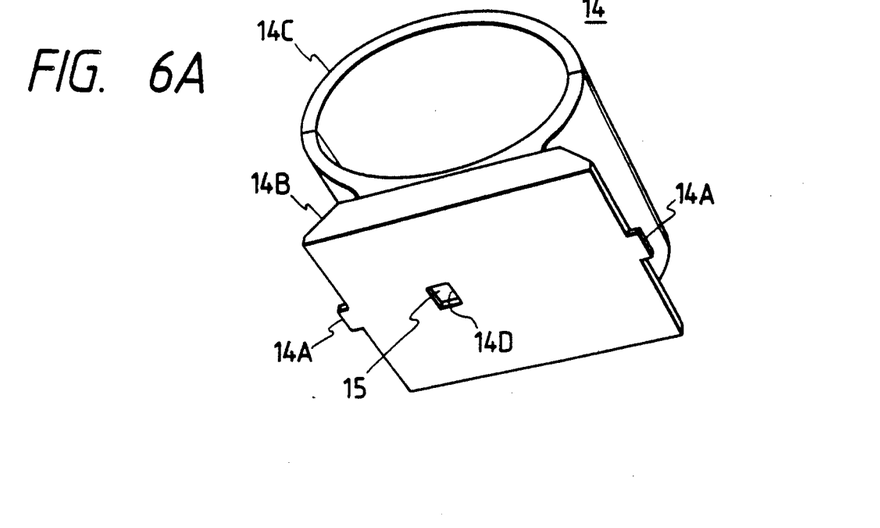
FIG. 6A is a perspective view of an RF coil unit for imaging a slice of the examinee's body in FIG. 3.
Figure 6B:
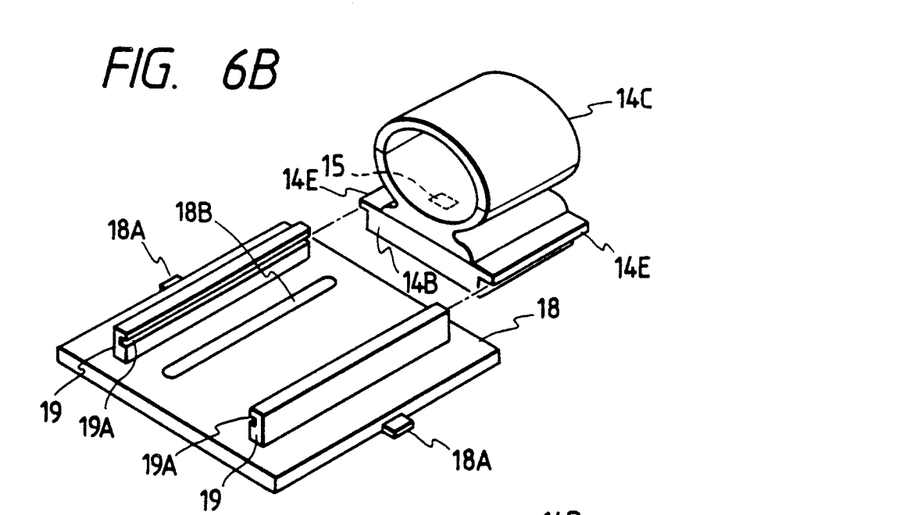
FIG. 6B is a perspective view of an RF coil unit for imaging a slice of the examinee's head in FIG. 3.
Figure 6C:
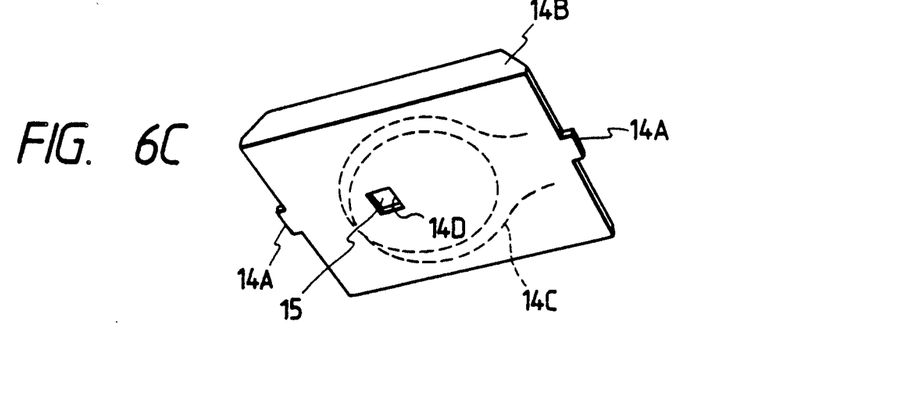
FIG. 6C is a perspective view of an RF coil unit for imaging the examinee's skin surface region in FIG. 3.
Figure 7:
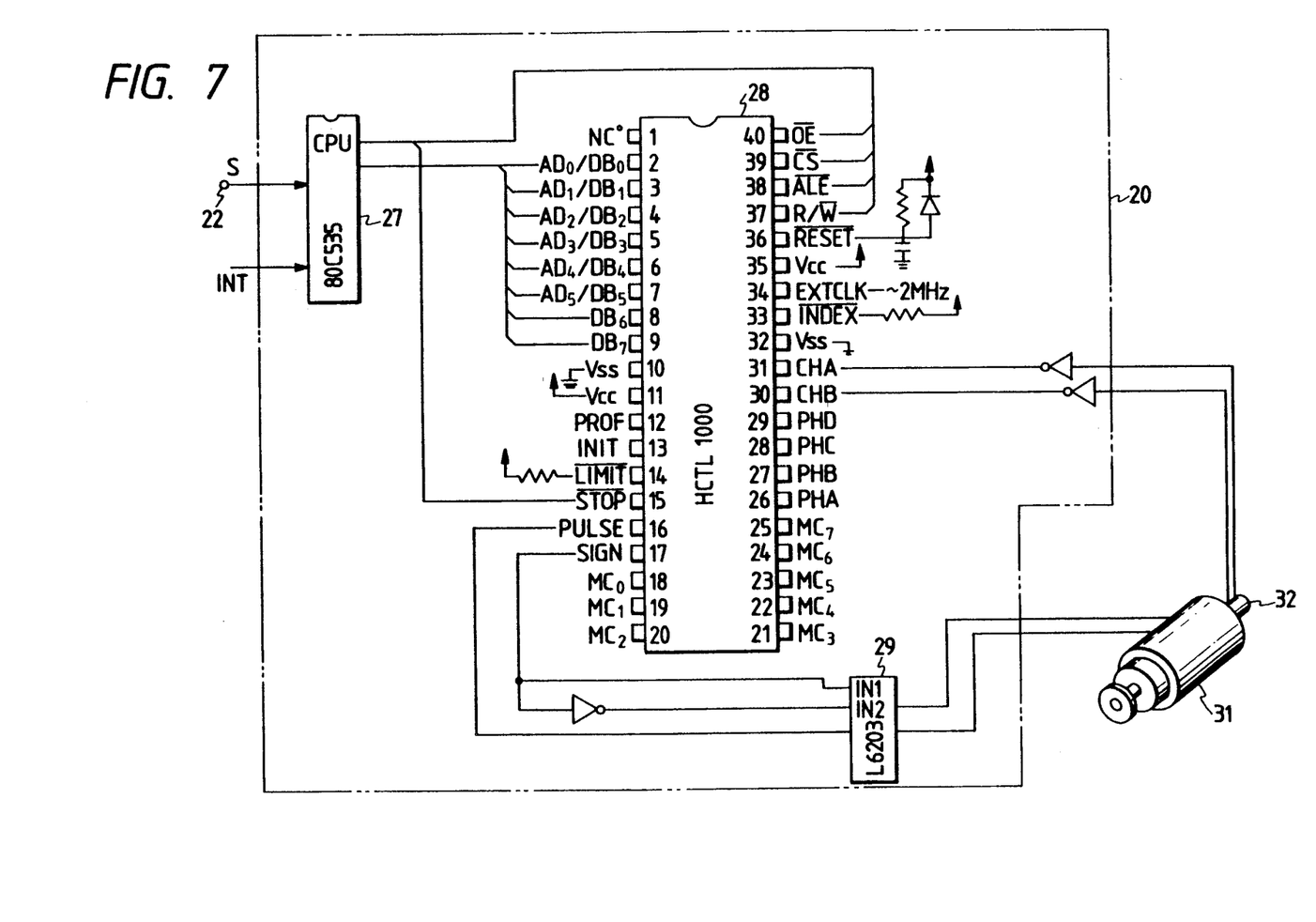
FIG. 7 is a block diagram of the pallet drive control unit for positioning the RF coil in FIG. 3.
Figure 8:
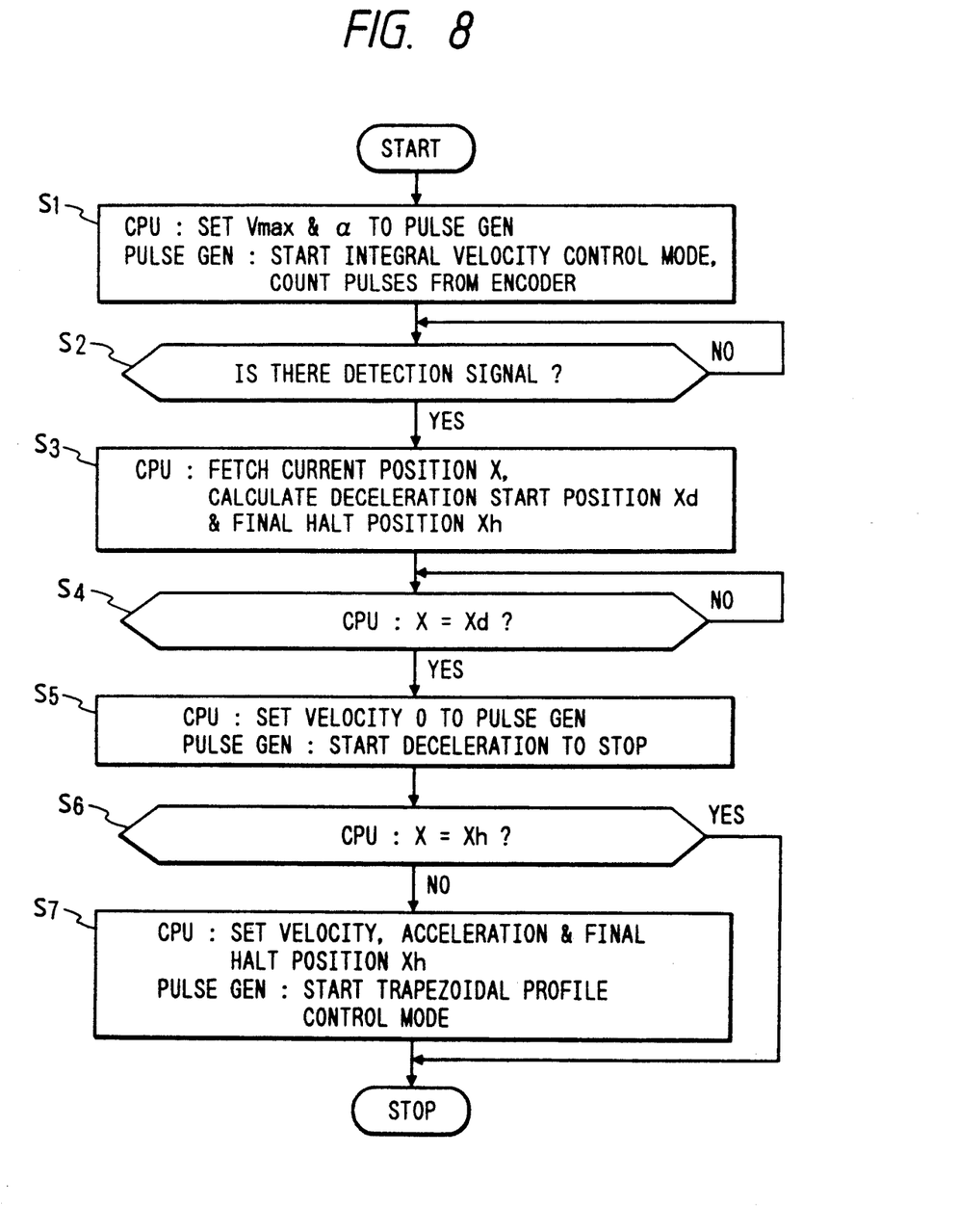
FIG. 8 is a flowchart of a pallet drive control operation in FIG. 7.
Figure 9:
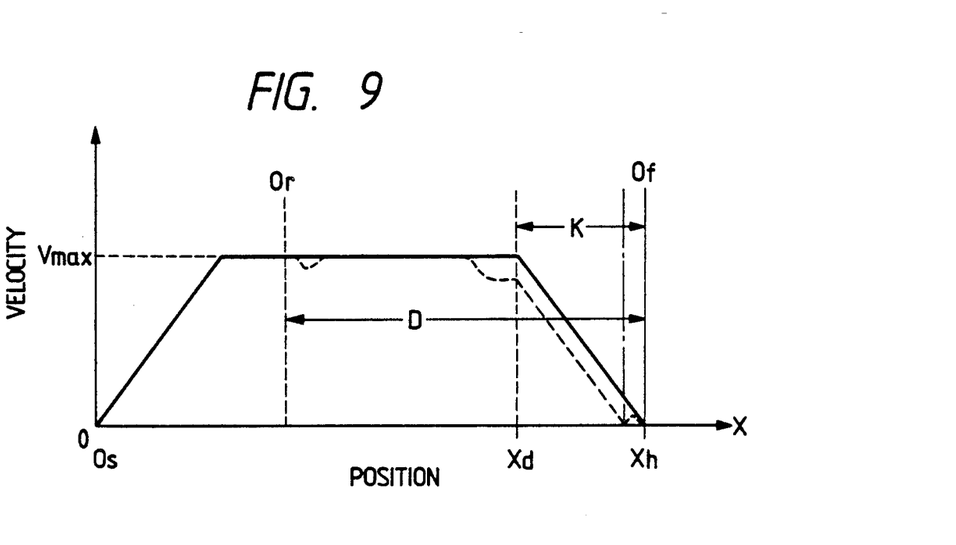
FIG. 9 is a graph showing, by way of example, velocity control by the control operation depicted in FIG. 8.

FIGS. 3 through 5 illustrate a specific operative example of the positioning device of the present invention. FIGS. 6A through 6C show three kinds of typical RF coil units for use in the device depicted in FIG. 3. FIGS. 7 through 9 depict a pallet drive unit for moving the pallet and examples of its control operation.

FIG. 3 is a perspective view showing the external appearance of the MRI device embodying the present invention. The parts corresponding to those in FIGS. 1 and 2 are identified by the same reference numerals. The magnetostatic field generator 12 is disposed adjacent the bed unit 10 lengthwise thereof (in the X-axis direction). The magnetostatic field generator 12 has the substantially columnar magnetic field compartment 12A which extends in alignment with the bed unit 10. In the magnetic field compartment 12A a magnetostatic field can be formed, for instance, at right angles to the lengthwise direction of the compartment 12A and horizontally (in the Z-axis direction).

FIG. 4 is a cross-sectional view of the bed unit 10 at the position adjacent the photoelectric sensor 16 and FIG. 5 a longitudinal sectional view of the bed unit 10 along the photoelectric sensor 16 and the slot window 13A. The bed unit 10 includes the mount 11 and the pallet 13. The mount 11 has posts 11C, lateral beams 11D and longitudinal beams 11E which form a frame, and upper and lower aluminum covers 11A and 11B covering the frame. The upper covers 11A have their both side portions raised and two support rails 11F are disposed in parallel to each other along the longitudinal beams 11E. The support rails 11F are fixed at both ends to end plates 11G which are provided at right angles thereto and fixed to both ends of the longitudinal beams 11E.

The pallet 13 is made as of FRP and has on its underside two rows of rollers 13C disposed at regular intervals lengthwise thereof in opposing relation to the top surfaces of the support rails 11F. Between the both upper covers 11F the pallet 13 is mounted on the rails 11F through the rollers 13C. The pallet 13 has a slot window 13A extending lengthwise thereof at a position corresponding to the photoelectric sensor 16 widthwise thereof (i.e. in the Z-axis direction). The photoelectric sensor 16, which emits light through the slot window 13A and detects light reflected back thereto from the mirror 14 mounted on the underside of the RF coil unit 14, is fixed to the upper lateral beam 11D. Plural pairs of recesses 13B selectable for positioning the RF coil unit 14 are formed at regular intervals along both inner marginal edges of the pallet 13 as shown in FIG. 3.

Two pulleys 11H are provided near both ends of the two support rails 11F intermediate therebetween, a toothed belt 33 being trained around the pulleys 11H. The toothed belt 33 is driven by a DC motor 31 through toothed drive wheel 11J and a toothed belt 11K.

FIG. 6A shows an example of the RF coil unit 14 for imaging a slice of the body, and the RF coil 14C is fixedly mounted on a trapezoidal coil base 14B in which an impedance matching circuit (not shown) of the RF coil is housed. The coil base 14B has engaging projections 14D at both marginal edges. In the underside of the coil base 14B a recess 14D, for example, 10 mm long, 20 mm wide and 2 mm deep, is formed at the position corresponding to the slot window 13A of the pallet 13 and a mirror adhesive seal of about the same size as the recess 14D and having a thickness of 0.5 mm is adhered to the bottom of the recess 14D, forming the reflecting mirror 15. The position of the mirror 15 is chosen so that the center position of the RF coil 14C in the axial direction agrees with the center or the front edge of the mirror 15.

FIG. 6B shows an example of the RF coil unit 14 for imaging a slice of the head. The RF coil 14C is fixedly mounted on a rectangular coil base 14B, in which an impedance matching circuit (not shown) is housed. The coil base 14B has sliding rims 14E laterally projecting out from its both marginal edges parallel to the longitudinal direction of the pallet 13. The sliding rims 14E are inserted in and guided by guide grooves 19A formed in inner side walls of parallel spaced-apart sliding rails 19 mounted on a square mount base 18. The reflecting mirror 15 is the same mirror seal as that described above in connection with FIG. 6A and it is adhered to the underside of the coil base 14B in alignment with the center of the coil 14C. The mount base 18 has engaging projections 18A at its both marginal edges and has, between the two sliding rails 19, a slot extending in the X-axis direction at the position corresponding to the mirror 15 in its widthwise direction (i.e. in the X-axis direction). The mount base 18 is mounted on the pallet 13, with the engaging projections 18A of the former received in a desired pair of positioning recesses 13B of the latter. The desired position of a slice of the examinee's head can be obtained by sliding the coil base 14B in the X-axis direction relative to the examinee's head inserted in the coil 14C, and this operation is easy. When the center of the RF coil 14C in the X-axis direction, that is, the center or the front edge of the mirror 15 has reached the reference position Or, light from the photoelectric sensor 16 passes through the slot window 13A of the pallet 13 and the slot 18B of the mount base 18 and is then reflected back by the mirror 15 and detected by the photoelectric sensor 16.

FIG. 6C shows a surface coil which is used for imaging a region near the skin surface, for example, the backbone, in the MRI device in which the magnetostatic field is produced in the horizontal direction (i.e. in the Z-axis direction) as shown in FIG. 3. The RF coil 14C is housed together with an impedance matching circuit (not shown) of the RF coil in a flat trapezoidal box-shaped coil base 14B. The coil base 14B has engaging projections 14A at its both marginal edges. The reflecting mirror seal 15 is adhered to the bottom of the recess 14D formed in the underside of the coil base 14B, in alignment with the center of the coil 14C. The coil base 14B is disposed on the pallet 13, with the engaging projections 14A of the former received in a desired pair of positioning recesses 13B of the latter. Since the examinee is allowed to lie on his back with the coil unit 14 held thereunder, the examinee can maintain his posture relatively easily during the transmission and reception of MR signals.

FIG. 7 illustrates a specific operative example of a pallet drive unit including the control circuit 20. This example employs, for instance, 80C535 of Siemens as the CPU 27, a motor control IC HCT-100 of YHP as the pulse generator 28 and L6203 of SGS as the motor driver 29. The above-mentioned control IC used as the pulse generator 28 has incorporated therein the counter 21 shown in FIG. 2. Next, the flowchart shown in FIG. 8 will be described with reference to FIGS. 7 and 9.

After the RF coil unit 14 of the kind to be used is fixed to a desired pair of the positioning recesses 13B of the pallet 13, the operator puts the examinee on the pallet 13 and moves the RF coil unit 14 and/or the examinee so that the region of the examinee's body to be imaged is positioned at the center of the RF coil unit 14. Then the operator presses a start button (not shown) to apply the start signal S to the CPU 27.

Step $S_1$: The CPU 27 responds to the start signal S to provide preknown values of a maximum velocity Vmax and an acceleration $\alpha$ of the pallet 13 to the pulse generator 28, i.e. the motor control IC. When supplied with the values of the velocity and acceleration, the control IC 28 immediately resets its internal counter to zero and, at the same time, starts an integral velocity control mode. That is, the frequency of control pulses to be applied to the driver 29 is controlled so that the moving speed of the pallet 13 increases from zero with a fixed acceleration u and the preset maximum velocity Vmax is maintained when it is reached. The rotary encoder 32 coupled with the DC motor 33 generates a pulse for each fixed rotational angle, and the pulse is counted by the internal counter of the control IC 28. The count value of the counter is sequentially updated and recorded as the current position X of the RF coil unit 14 in an actual position register provided in the control IC 28.

Step $S_2$: Upon starting of the integral velocity control by step $S_1$, the CPU 27 always monitors as to whether a detection signal INT is yielded from the photoelectric sensor 16. When the pallet 13 moves and the reflecting mirror 15 of the RF coil unit 14 passes through the reference position Or, the photoelectric sensor 16 outputs a detection signal INT, and the CPU 27 responds to the detection signal INT to execute the next step.

Step $S_3$: In response to the detection signal INT the CPU 27 fetches the contents of the actual position register in the control IC 28, that is, the current position X of the RF coil unit 14, calculates the distance Xd from the initial position Os to a predetermined deceleration start position and the distance Xh from the initial position Os to the halt position Of by using the following equations, respectively, and stores the calculated values in its internal memory.

$$Xd = X + D - K$$

$$Xh = X + D$$

where D is the distance from the reference position Os to the final halt position, that is, the center Of of the magnetic field compartment 12A, and K is the distance of travel in the case where the velocity of travel is decelerated from the maximum velocity Vmax to zero at the predetermined acceleration $\alpha$. The former is premeasured and the latter is precalculated, and they are prestored in the CPU 27.

Step S₄: The CPU 27 compares the current position X fetched from the control IC 28 with a fixed cycle and the precalculated deceleration start position Xd, and when the current position X becomes equal to the deceleration start position Xd, the process proceeds to the next step.

Step S₅: The CPU 27 provides the value of a velocity 0 to the control IC 28, and the control IC 28 controls the driver 29 so that it decelerates the motor 33 at the acceleration $\alpha$ toward the velocity 0, by which the motor 33 gradually decelerated until it is stopped.

Even if the integral velocity control using the preset velocity and acceleration, the velocity of travel may sometimes becomes lower than the preset velocity Vmax as indicated by the broken line in FIG. 9 owing to load variations during travel. Where the actual velocity is lower than the preset value at the deceleration start position Xd, the RF coil unit 14 stops before reaching the final halt position Of. Accordingly, this embodiment further performs the following steps:

Step S₆: The CPU 27 compares the actual halt position X and the precalculated final halt position Xh and, if they coincide, the CPU 27 judges that the RF coil unit 14 has accurately been positioned, and completes the control operation. When the current position X and the final halt position Xh are not equal to each other, the CPU 27 judges that the RF coil 14 has not yet reached the final halt position Of, and proceeds to the following position correcting step:

Step S₇: The CPU 27 provides values of the final halt position Xh and the predetermined velocity and acceleration to the control IC 28. Based on these values supplied thereto the control IC 28 calculates a necessary velocity profile from the current halt position to the final one and starts a trapezoidal profile control mode in accordance with the calculated velocity profile, thereafter completing its operation. In the travel from the current halt position to the final halt position in this mode, if the preset velocity is not reached when the RF coil unit 14 has reached a position one-half of the distance to the final halt position, the velocity profile will not become trapezoidal but triangular as shown in FIG. 9.

The equations expressing the deceleration start position Xd and the final halt position Xh mentioned previously in step S₃ are used in the case of employing the RF coil unit 14 in which the front edge of the reflecting mirror 15 is set at the center of the RF coil 14C in its axial direction. In the case of using the RF coil unit 14 of the type that the center of the RF coil 14C in its axial direction is set at the center of the mirror 15, the positions Xd and Xh can be expressed as follows:

$$Xd = X + (A/2) + D - K$$

$$Xh = X + (A/2) + D$$

where A is the length of the mirror 15 in the direction of travel (in the X-axis direction).

As described above, according to the present invention, in the case of moving the RF coil unit from the initial position to the imaging position in the magnetostatic field, there is no need of manual operation of stopping the pallet carrying the examinee and positioning the center of the RF coil in alignment with the optical marker. Accordingly, the RF coil can be easily and accurately moved to the imaging position in a short time without suffering from an error in manual positioning by the operator.

It will be apparent that many modifications and variations may be effected without departing from the scope of the novel concepts of the present invention.

What is claimed is:

1. An RF coil positioning device for MRI in which a pallet movably mounted on a mount is moved by drive means so that an RF coil unit mounted on said pallet is moved from its initial positioned at an imaging position in a magnetostatic field generator, said coil positioning device comprising:
   coil detecting means provided at a predetermined position along a path of said pallet, for detecting the passage of said RF coil unit through a reference position on said path and generating a detection signal, the distance between said reference position and said imaging position being preknown;
   distance detecting means for detecting the distance of travel of said pallet; and
   drive control means supplied with signals from said coil detecting means and said distance detecting means, for controlling said drive means to move said pallet until the distance of its travel after the generation of said detection signal becomes equal to the distance from said reference position to said imaging position;
   wherein said coil detecting means is provided below the underside of said pallet.

2. The RF coil positioning device of claim 1, wherein said drive means is a motor means.

3. The RF coil positioning device of claim 1, wherein said coil detecting means includes a reflection type photoelectric sensor and said pallet has a light-transparent window made therein at a position opposite at least the underside of said RF coil unit.

4. The RF coil positioning device of claim 3, wherein a reflecting mirror is mounted downward on the underside of the RF coil unit.

5. The RF coil positioning device of claim 1, wherein said coil detecting means is mounted on said mount outside said magnetostatic field generator.

6. The RF coil positioning device of claim 4, wherein said RF coil unit includes a coil base and an RF coil fixedly mounted thereon and said reflecting mirror is mounted on the underside of said coil base.

7. The RF coil positioning device of claim 1, wherein said RF coil unit is mounted on said pallet in such a manner that its position can be varied lengthwise of said pallet.

8. The RF coil positioning device of claim 7, wherein said RF coil unit can be mounted on said pallet at regular intervals lengthwise thereof.

9. The RF coil positioning device of claim 8, wherein a plurality of pairs of positioning means for defining the position where to mount said RF coil unit on said pallet are provided at regular intervals along both sides of said pallet lengthwise thereof.

10. The RF coil positioning device of claim 1, wherein said RF coil unit includes a coil base, an RF coil fixedly mounted thereon, and a reflecting mirror mounted downward on the underside of said coil base.

11. The RF coil positioning device of claim 1, wherein said RF coil unit includes a flat coil base, an RF coil housed therein, and a reflecting mirror mounted downward on the underside of said coil base.

12. The RF coil positioning device of claim 1, wherein said RF coil unit includes a coil base, an RF coil fixedly mounted thereon, a mount base having slidably mounted thereon said coil base, and a reflecting mirror mounted downward on the underside of said coil base, said mount base having a slot formed therein at the position corresponding to said reflecting mirror and extending in the direction of sliding of said coil base.

13. An RF coil positioning device for MRI in which a pallet slidably mounted on a mount is moved by motor means so that an RF coil mounted on said pallet is moved from its initial position to and positioned at an imaging position in a magnetostatic field generator, said coil positioning device comprising:

coil detecting means provided at a predetermined position along a path of said pallet, for detecting the passage of said RF coil unit through a reference position on said path and generating a detection signal, the distance between said reference position and said imaging position being preknown;

distance detecting means for detecting the distance of travel of said pallet; and drive control means which obtains from said distance detecting means the distance of travel of said pallet to the time point of the generation of said detection signal, calculates the distance of travel of said pallet from its initial position to said imaging position on the basis of said distance of travel obtained from said distance detecting means and said preknown distance, and controlling the drive of said motor means to move said pallet to said imaging position;

wherein said coil detecting means is provided below the underside of said pallet.

14. The RF coil positioning device of claim 13, wherein said coil detecting means includes a reflection type photoelectric sensor, said RF coil unit has a reflecting mirror mounted downward on the underside thereof, and said pallet has a light-transparent window formed therein facing the underside of said RF coil unit.

15. The RF coil positioning device of claim 13, wherein said coil detecting means is mounted on said mount outside said magnetostatic field generator.

16. The RF coil positioning device of claim 13, wherein said RF coil unit is mounted on said pallet in such a manner that its position can be varied lengthwise of said pallet.

17. The RF coil positioning device of claim 13, wherein said RF coil unit can be mounted on said pallet at regular intervals lengthwise thereof.

18. The RF coil positioning device of claim 13, wherein said distance detecting means includes encoder means, coupled with said motor means, for generating a pulse for each unitary rotational angle of said motor means, and wherein said drive control means includes: counter means for counting pulses from said encoder means; a CPU responsive to said detection signal from said coil detecting means to read out the count value of said counter means and to calculate the distance of travel of said pallet based on said count value and said preknown distance from said reference position to said imaging position; control pulse generating means for controlling the drive of said motor means based on the distance of travel provided from said CPU; and driver means for driving said motor means in response to said control pulse from said control pulse generating means.

* * * * *